United States Patent [19]

Neurath et al.

[11] Patent Number: 5,798,206
[45] Date of Patent: Aug. 25, 1998

[54] METHODS FOR SCREENING OF TEST COMPOUNDS FOR INHIBITING BINDING OF A CD4-HIV 1 COMPLEX TO A CHEMOKINE RECEPTOR

[75] Inventors: Alexander Robert Neurath; Asim Kumar Debnath, both of New York; Shibo Jiang, Jackson Heights; Yun-Yao Li, Flushing; Nathan Strick, Oceanside, all of N.Y.

[73] Assignee: New York Blood Center, New York, N.Y.

[21] Appl. No.: 782,044

[22] Filed: Jan. 10, 1997

[51] Int. Cl.$^6$ ............................. C12Q 1/70; G01N 33/53
[52] U.S. Cl. ............................. 435/5; 435/7.1; 435/7.2; 435/7.24
[58] Field of Search ........................ 435/4, 5, 7.1, 7.2, 435/7.24

[56] References Cited

U.S. PATENT DOCUMENTS

| | | | |
|---|---|---|---|
| 5,158,871 | 10/1992 | Rossomando et al. | 435/7.32 |
| 5,411,863 | 5/1995 | Miltenyi | 435/6 |

OTHER PUBLICATIONS

Premack, B.A. anad Schall, T.J., "Chemokine Receptors: Gateways to Inflammation and Infection", Nature Medicine, 2, 1174–1178 (1996).

Zhang, L., Huang, Y., He, T., Cao, Y. and Ho, D.D., "HIV-1 Subtype and Second-Receptor Use", Nature, 383, 768 (1996).

Huang, Y. et al., "The Role of a Mutant CCR5 Allele in HIV-1 Transmission and Disease Progression", Nature Medicine, 2, 1240–1243 (1996).

Lapham, C.K. et al., "Evidence for Cell–Surface Association Between Fusin and the CD4–gp120 Complex in Human Cell Lines", Science, 274, 602–605 (1996).

Arenzana–Seladedos, F. et al., "HIV Blocked by Chemokine Antagonist", Nature, 383, 400 (1996).

Causey, L.D. and Dwyer, D.S., "Detection of Low Affinity Interactions Between Peptides and Heat Shock Proteins by Chemiluminescence of Enhanced Avidity Reactions (CLEAR)", Nature Biotech., 14, 348–351 (1996).

Neurath, A.R., Jiang, S., Strick, N., Lin, K., Li, Y-Y. and Debnath, A.K., "Bovine β–Lactoglobulin Modified by 3–Hydroxyphthalic Anhydride Blocks the CD4 Cell Receptor for HIV", Nature Medicine, 2, 230–234 (1996).

Neurath, A.R., Strick, N. and Debnath, A.K., "Structural Requirements for and Consequences of an Antiviral Porphyrin Binding to the V3 Loop of the Human Immunodeficiency Virus (HIV-1) Envelop Glycoprotein gp120", J. Mol. Recognition, 8, 345–357 (1995).

Cocchi, F. et al., "V3 Domain of HIV-1 Envelope Glycoprotein gp120 is Critical for Chemokine-Mediated Blockade of Infection", Nature Med., 2, 1244–1247 (1996).

Deng, H.K. et al., "Identification of a Major Co-receptor for Primary Isolates of HIV-1", Nature, 381, 661–666 (1996).

Deng et al., 1996, Nature 381:661–666.

Neurath et al., 1996, Nature Med. 2:230–234.

Causey et al., 1996, Nature Biotech. 14:348–351.

Immunotech, 1995, Antibodies and Immunoassays Product and Price list, Immunotech, Inc.

Primary Examiner—Laurie Scheiner
Assistant Examiner—Jeffrey S. Parkin
Attorney, Agent, or Firm—Frishauf, Holtz, Goodman, Langer & Chick, P.C.

[57] ABSTRACT

A method for the screening of a test compound for inhibiting the binding of a CD4-HIV 1 complex to HIV-1 second receptors, comprising: (a) preparing a magnetic ligand by mixing a magnetic, CD4-containing substrate with HIV-1, (b) mixing the magnetic ligand from step (a) with a test compound, (c) adding cells that express the HIV-1 second receptors to the mixture from step (b), (d) separating cells with bound magnetic ligands from cells without bound magnetic ligands by contact with a magnetic separator, and (e) quantifying the cells with bound magnetic ligands and quantifying the cells without bound magnetic ligands.

17 Claims, 1 Drawing Sheet

METHODS FOR SCREENING OF TEST COMPOUNDS FOR INHIBITING BINDING OF A CD4-HIV 1 COMPLEX TO A CHEMOKINE RECEPTOR

GOVERNMENT RIGHTS

This invention was made with United States Government support under Grant CA 43315 from the National Institutes of Health. Accordingly, the United States Government has certain rights in this invention.

BACKGROUND OF THE INVENTION

1. Field of the Invention

The present invention concerns a method for screening of test compounds for inhibiting binding of a CD4-HIV 1 complex to HIV-1 second receptors.

2. Background Information

The α-chemokine receptor (α-ChR) CXCR4/LESTR/Fusin has been recently identified as a cofactor for entry of T-cell line tropic HIV-1 into CD4+T cells, while the β-ChRs, CR-5, CCR-3 and CCR-2b have been identified as cofactors for infection with macrophage-tropic and primary HIV-1 isolates (Premack, B. A. and Schall, T. J., "Chemokine Receptors: Gateways to Inflammation and Infection", *Nature Medicine*, 2, 1174–1178 (1996); and Zhang, L., Huang, Y., He, T., Cao, Y. and Ho, D. D., "HIV-1 Subtype and Second-Receptor Use", *Nature*, 383, 768 (1996)).

The α-chemokine SDF-1 and the β-chemokines RANTES, MIP-1α and MIP-1β block infection by HIV-1 with the two distinct cell tropisms. A 32-nucleotide deletion within the CCR5 gene has been described in subjects who remained uninfected despite repeated exposures to HIV-1 (Huang, Y. et al., "The Role of a Mutant CCR5 Allele in HIV-1 Transmission and Disease Progression", *Nature Medicine*, 2, 1240–1243 (1996).

Evidence for the physical association between CXCR4 and CD4-HIV-1 envelope glycoprotein gp120 complexes on cell membranes has been reported (Lapham, C. K. et al., "Evidence for Cell-Surface Association Between Fusin and the CD4-gp120 Complex in Human Cell Lines", *Science*, 274, 602–605 (1996)).

Receptor signaling and cell activation are probably not required for the anti-HIV-1 effect of chemokines since a RANTES analog lacking the first eight N-terminal amino acids, RANTES (9–68), lacked chemotactic and leukocyte-activating properties, but bound to multiple β-ChRs and inhibited infection by macrophage-tropic HIV-1 (Arenzana-Seladedos, F. et al., "HIV Blocked by Chemokine Antagonist", *Nature*, 383, 400 (1996)).

Cumulatively, the above described results suggest that interactions between HIV-1 gp120 (or its complexes with CD4) and the respective ChRs are obligatory for HIV-1 infection, but evidence for direct binding of extracellular virions to these ChRs has been lacking.

The ChRs functioning as cofactors for HIV infection belong to the class of seven transmembrane proteins. These hydrophobic membrane constituents, even if expressed as recombinant envelope glycoproteins, are difficult to purify and may not be suitable for the development of techniques for measuring ChR-chemokine or ChR-HIV-1 binding, which instead have to rely on the use of cells expressing these proteins. Ligand-receptor interactions that are of low affinity or occur at very low concentrations of reactants are difficult to measure by straightforward binding measurements. Methods based on the generation of multivalent ligands with increased binding avidity to measure such interactions were developed recently (Causey, L. D. and Dwyer, D. S., "Detection of Low Affinity Interactions Between Peptides and Heat Shock Proteins by Chemiluminescence of Enhanced Avidity Reactions (CLEAR)", *Nature Biotech.*, 14, 348–351 (1996)).

SUMMARY OF THE INVENTION

An object of the present invention is to furnish a method for the screening of a test compound for inhibiting the binding of a CD4-HIV-1 complex to HIV-1 second receptors.

The aforesaid object is satisfied by the present invention which provides a method comprising: (a) preparing a magnetic ligand by mixing a magnetic, CD4-containing substrate with HIV-1, (b) mixing the magnetic ligand from step (a) with a test compound, (c) adding cells that express the HIV-1 second receptors to the mixture from step (b), (d) separating cells with bound magnetic ligands from cells without bound ligands by contact with a magnetic separator, and (e) quantifying the cells with bound magnetic ligands and quantifying the cells without bound magnetic ligands.

BRIEF DESCRIPTION OF THE DRAWING

The FIGURE is a bar graph showing a ratio of cells with bound ligand/cells without bound ligand.

DETAILED DESCRIPTION OF THE INVENTION

Figure 1:
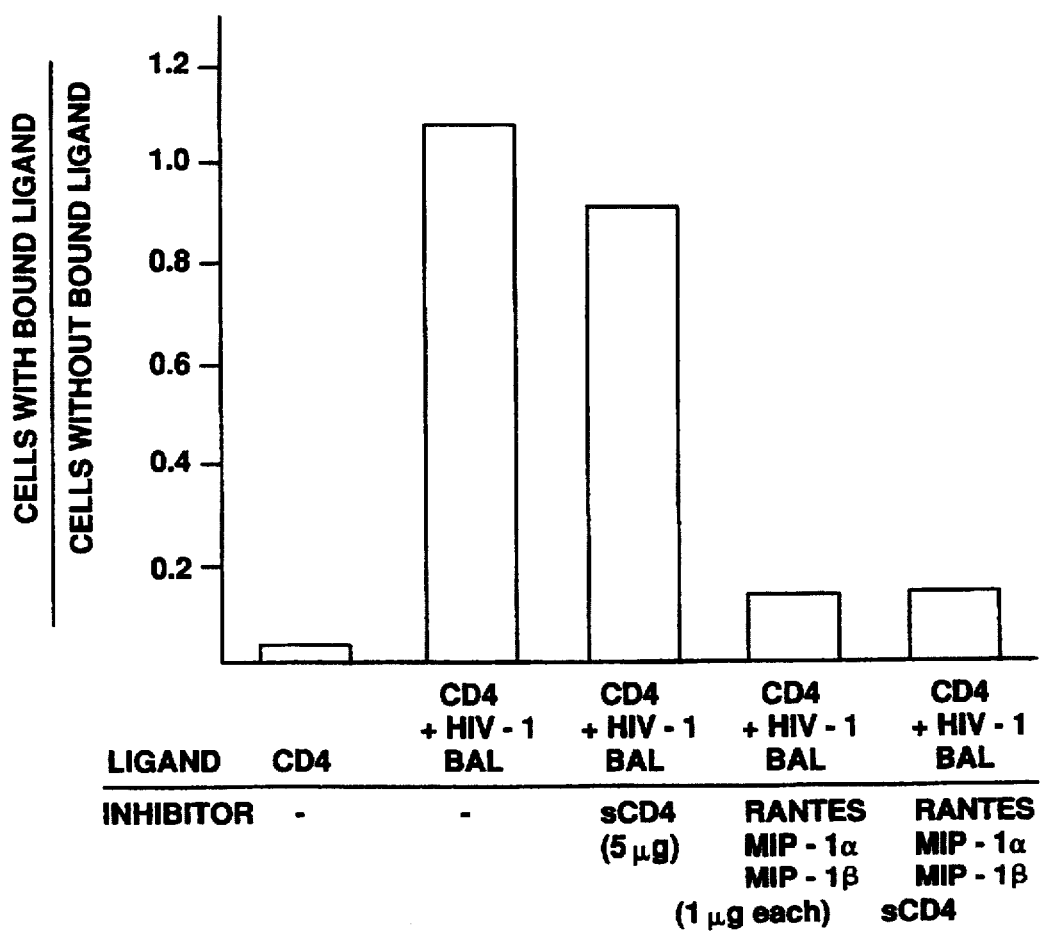

The magnetic, CD4-containing substrate is preferably a magnetic, CD4-containing particle such as a bead, i.e., a CD4 magnetic bead. The magnetic bead is, for example, a paramagnetic divinyl benzene bead. The magnetic particle portion of the bead can have the following characteristics: an iron concentration of about 18.2 to 18.9 mg/ml; a solids concentration of about 30.5 to 30.6 mg/ml; magnetics: about 37.9 to 41.1 EMU/g; and a size of about 700 nm (NICOMP measurement).

The magnetic separator preferably comprises permanent magnets enclosed in a plastic frame which can accommodate 96-well plates.

Typical separation time is one to ten minutes depending upon the volume of magnetic particles used. Once separation is complete, the 96-well plate should be kept in position over the magnetic separator and the supernatant should be removed slowly. The pipette should be positioned as far away from the magnetic pellet as possible to avoid disturbing the magnetic pellet.

To wash the magnetic particles, the supernatant should be slowly removed with the pipette, while the magnet is still in place. The 96-well plate should then be removed from the magnet and an appropriate volume of wash buffer should be added. The plate should be tapped gently to mix the magnetic particles and the 96-well plate should be repositioned over the magnet for one to ten minutes, or until a firm magnetic pellet is formed.

The quantification of cells with bound magnetic ligands and cells without bound magnetic ligands can be performed by known detection methods such as fluorometrically or enzymatically.

The cells can be quantitated either enzymatically, for example, by measuring lactate dehydrogenase (LDH) activity as described in Neurath, A. R. et al., "Bovine β-Lactoglobulin Modified by 3-Hydroxyphthalic Anhydride Blocks the CD4 Cell Receptor for HIV", *Nature Medicine*, 2, 230–234 (1996) or fluorometrically, for example, by using the ("CyQUANT"™ Assay Kit (Molecular Probes, Inc., Eugene, Oreg.), with similar results.

The proportion of attached and unattached cells can be determined by measurements of lactate dehydrogenase (LDH) activity in aliquots of cell lysates obtained after exposure of the cells to the detergent Triton X-100 (5 mg/ml in $H_2O$). LDH can be determined using the Sigma No. 500 diagnostic kit. The standard deviation of relative cell counts obtained by this method is ±8%.

Alternatively the cells can be quantitated fluorometrically by using the CyQUANT™ Cell Proliferation Assay Kit, which provides a rapid and sensitive procedure for determining the density of cells in culture. The assay has a linear detection range extending from 50 or fewer to at least 50,000 cells in 200 µL volumes and thus can be used for cell proliferation studies, as well as for routine cell counts. The CyQUANT assay can detect much lower cell numbers than Neutral Red or methylene blue assays. Unlike procedures that rely on the conversion of tetrazolium dyes to blue formazan products or on $^3H$ thymidine incorporation assays, the CyQUANT method is rapid and does not rely on cellular metabolic activity. Thus, cells must be frozen prior to assaying and can be kept frozen prior to assays up to 4 weeks at −70° C.; time course assays are facile and data obtained from samples taken at widely different time intervals can be directly compared. The basis for the CyQUANT assay is the use of a green fluorescent dye, CyQUANT™-GR, that exhibits strong fluorescence enhancement when bound to cellular nucleic acids. Cells are lysed by addition of a buffer containing the CyQUANT-GR dye; fluorescence is then measured directly. There are no washing steps, growth medium changes or long incubations.

The materials included in the CyQUANT Cell Proliferation Assay Kit include the following:

(1) 550 µL of CyQUANT-GR (Component A), 400× concentrate in DMSO. For CyQUANT-GR bound to nucleic acids, the excitation maximum is about 480 nm and the emission maximum is about 520 nm.

(2) 11 mL of cell lysis buffer, 20×concentrate (Component B).

(3) 100 µL×DNA standard, 100 µg/mL in TE (Tris/EDTA) buffer (Component C).

Reagent preparation for the CYQUANT Cell Proliferation Assay is carried out as follows:

The concentrated cell lysis buffer stock solution (Component B) is diluted 20-fold in distilled water. For each assay, 200 µL are required. Just prior to running the experiment, the CyQUANT-GR stock solution (Component A) is diluted 400-fold into the 1×cell lysis buffer. For example, to prepare 20 mL of CyQUANT-GR working solution (enough for about 100 assays), the 1×cell lysis buffer is made first by mixing 1 mL of the 20×stock with 19 mL of nuclease-free distilled water; next 50 µL of the CYQUANT-GR stock solution is added and the resultant mixture is mixed thoroughly.

The working solution should be protected from light by keeping it in an opaque bottle, covering it with foil or placing it in the dark to prevent photo-degradation of the CyQUANT-GR dye. For best results, the solution should be used within a few hours of its preparation.

A reference standard curve can be created for converting sample fluorescence values into cell numbers as follows (the cell type used for the standard curve should be the same as that which is used in the experiment):

(1) Prepare a concentrated cell suspension in medium: ideally this should be about 1 mL total volume at a density of about $10^5$ to $10^6$ cells/mL. Determine the actual cell density by counting the cells using a hemacytometer.

(2) Centrifuge 1.0 mL of the concentrated cell suspension for 5 minutes at 200×g (1500 rpm in a microcentrifuge). Remove and discard the supernatant without disturbing the cell pellet, and freeze the cell pellet at −70° C.

(3) Thaw the cell pellet at room temperature, add 1.0 mL of the CyQUANT-GR/lysis buffer prepared as described above and resuspend the cells by briefly vortexing.

(4) Generate a dilution series in the wells of a microtiter plate. Use the CyQUANT-GR/lysis buffer and make dilutions corresponding to cell numbers ranging from 50 to 50,000 in 200 µL volumes. Include a 200 µL sample with no cells as a control. Incubate for 2 to 5 minutes at room temperature (protected from light).

(5) Measure the fluorescence of the samples using a fluorescence microtiter plate reader (such as the PerSeptive Biosystems, Inc., Cambridge, Mass., CytoFluor™ 2350) set up with appropriate excitation and emission filters. The excitation maximum is about 480 nm; the emission maximum is about 520 nm.

The CyQUANT Cell Proliferation Assay Kit can be used to carry out the following assays and determinations:

1. Cells Proliferation Assay; Adherent Cells Grown in Microtiter Plates (a) Make a concentrated cell suspension in growth medium.

(b) Prepare serial dilutions in the wells of a microtiter plate such that 200 µL volumes of growth medium contain cell numbers ranging from 50 to 50,000. Include a control well with no cells. If a time course is desired, prepare duplicate dilutions in separate microtiter plates.

(c) Incubate the plate at 37° C. for a time sufficient to allow the cells to attach (typically, 4 to 16 hours); incubate longer to follow cell proliferation. For long-term proliferation studies, 100 µL of media should be removed from each well every other day and replaced with media.

(d) At the desired time, gently invert the microtiter plate, and blot it onto paper towels to remove media from the wells. The wells may be washed with PBS, but this is not essential, and is not recommended for very dense cultures where cells may dislodge. Freeze the cell pellets, and store the microtiter plate at −70° C. until samples are assayed.

(e) When ready to quantitate the samples, thaw the plates at room temperature, then add 200 µL of the CYQUANT-GR/lysis buffer (prepared as described above) to each sample well. Mix gently, if desired (generally not necessary). Incubate for 2 to 5 minutes at room temperature (protected from light).

(f) Measure the sample fluorescence using a fluorescence microtiter plate reader with filters appropriate for 480 nm excitation and 520 nm emission.

2. Cell Proliferation Assay: Suspension Cells Grown in Microtiter Plates.

The above procedure can be adapted for suspension cells if a centrifuge capable of centrifuging microtiter plates is available. Incubate the plates at 37° C. on a shaker platform with constant agitation. Whenever media changes are required, centrifuge the plate at a speed and time sufficient to pellet the cells. Remove the old medium and replace it with fresh medium. At the desired time point, centrifuge the plate, invert, blot to remove the medium, and freeze at −70° C. Analyze for adherent cells.

3. Cell-Number Determination: Cells Grown in Standard Culture Conditions

The CyQUANT Cell Proliferation Assay Kit can be used to count the number of cells in a sample taken from a conventional cell culture. For cultures of adherent cells, the cells must first be detached and suspended. Cells grown in suspension can be assayed directly.

(a) Transfer the sample of the suspended cells to a centrifuge tube and centrifuge for 5 minutes at 200×g (e.g., 1500 rpm in a microcentrifuge). The sample should contain from about 50 to about 50,000 cells. Remove and discard the supernatant without disturbing the cell pellet, and freeze the cell pellet at −70° C.

(b) Thaw the cell pellet at room temperature and add 200 µL of CyQUANT-GR/lysis buffer (prepared as described above).

(c) Transfer the entire 200 µL sample to a microtiter plate and measure the fluorescence. Convert the observed fluorescence to a cell number using a standard curve (see above). Many different cell types can be assayed using this procedure, but the absolute signal is cell type-dependent. Thus it is advisable to use a standard curve generated from the same cell type that is being assayed, for comparison. Alternatively, a standard curve generated using pure DNA can be calibrated relative to an appropriate cell type.

4. Cell Number Determination Based on DNA or RNA Alone

In the protocols described above, the CyQUANT-GR reagent is used to determine cell number by staining nucleic acids, both DNA and RNA. DNA to RNA ratios, however, may vary according to cell type and cell cycle. Fluorescence due to CyQUANT-GR binding to RNA can be eliminated by pretreating samples with DNase-free RNase.

(a) For determination of total cellular DNA or RNA, freeze a cell pellet containing 20,000 to 100,000 cells at −70° C., thaw at room temperature, and resuspend in a small volume (50–100 µL for microtiter plate assays) of 1×cell lysis buffer, containing 180 mM NaCl. For RNase treatment, this buffer should also contain 1 mM EDTA. For DNase treatment the buffer should contain 1 mM $CaCl_2$ and 1 mM $MgCl_2$.

(b) DNase-free-RNase A or RNase-free-DNase I is added to a final concentration of about 1.35 Kunitz units/mL (RNase) or 45 Kunitz units/mL (DNase). Samples are incubated for one hour at room temperature.

(c) An equal volume of a 2×solution of CYQUANT-GR dye diluted in cell lysis buffer (double the concentration of CYQUANT-GR dye described above) is added to each sample. Samples are incubated for 2 to 5 minutes.

(d) The fluorescence is measured as described above. It is desirable that controls be run for each digested sample, using the appropriate buffer, as the presence of salt and divalent cations slightly reduces the slope of the standard curve.

5. DNA Standard Curve

The CyQUANT Cell proliferation Assay Kit includes a 100 µg/mL sample of bacteriophage λ DNA (Component C) that can be used to prepare a standard curve for DNA content. The standard curve can serve to quantitate cellular DNA, provided the cell lysates are pretreated with DNase-free RNase to eliminate the RNA component of the fluorescent signal. Alternatively, the standard curve can be used to calibrate the assay for use of the same fluorometer or microtiter plate reader at different times or on different days. Variation in the signal intensity of the standard curve is directly related to variation that will be observed for assaying cells on different days, and is instrument-dependent. Prepare serially diluted 200 µL samples of bacteriophage λ DNA using CyQUANT-GR/lysis buffer (prepared as described above) with concentrations ranging from 50 pg/mL to 0.5 µg/mL in the wells of a microtiter plate. Include also a control well without DNA, and scan for fluorescence using a filter combination for excitation at about 480 nm and emission at about 520 nm.

An embodiment of the present invention provides for direct binding of HIV-1 (complexed with CD4) to ChR obtained by a new method—multivalent magnetic fluorescent enhanced avidity reaction ("MUMFEAR"). This method also allows high-throughput screening for compounds inhibiting binding. The interaction of macrophage-tropic HIV-1 Bal coated magnetic beads (instead of HIV-1 Bal, HIV-1 Ada-M or T lymphocyte tropic HIV IIIB can be used) with PM-1 cells was inhibited by RANTES/MIP-1α/MIP-1β.

The present invention is expected to contribute to exploiting the recent discovery of "second receptors" for HIV for development of new prevention and treatment strategies against AIDS by providing a rapid prescreening method for compounds inhibiting HIV-1 binding to the "second receptor".

EXAMPLE

The FIGURE shows chemokine inhibitable interaction between ChR expressing cells and magnetic CD4-HIV-1 complexes. The magnetic ligand was prepared by mixing ≈$5 \times 10^8$ CD4 magnetic beads (0.7µ diameter; $10^4$ CD4 molecules per bead) (ImmunoDiagnostics, Bedford, Mass.) with 1 mL of macrophage-tropic HIV-1 Bal (concentration corresponding to 4.2 ng/mL of the p24 nucleocapsid antigen) prepared by growing the virus in human peripheral blood monocytes. After 1.5 hours at 25° C., the beads were removed in a magnetic field and washed. $10^7$ Beads and control CD4 beads without HIV, respectively, were mixed with $10^5$ PM-1 cells expressing CD4 and receptors for RANTES/MIP-1α/MIP-1β (Ref. 29 cited in Premack et al., supra) in the presence and absence of inhibitors (the β-chemokines were obtained from R & D Systems, Minneapolis, Minn.) listed on the abscissa of the FIGURE.

After 1 hour at 25° C., the cells with the attached magnetic ligand were separated from ligand-free cells using appropriate BioMag separators (PerSeptive Biosystems, Framingham, Mass.).

The cells were quantitated by using the "CyQUANT"™ Assay Kit and an assay was carried out with $10^6$ beads and 50 to 20,000 cells in 96-well plates using the CytoFluor 2350 Fluorescence Measurement System (Millipore, Bedford, Mass.).

Interaction of the cells with HIV-1 magnetic ligands was inhibited by porphyrins (shown earlier to bind to the gp120 V3 loop (Neurath, A. R., Strick, N. and Debnath, A. K., "Structural Requirements for and Consequences of an Antiviral Porphyrin Binding to the V3 Loop of the Human Immunodeficiency Virus (HIV1) Envelope Glycoprotein gp120", J. Mol. Recognition, 8, 345–357 (1995)); data not shown), in agreement with the described role of the V3 loop in HIV-1-ChR interactions (Ref. 25 cited in Premack et al., supra).

It will be appreciated that the instant specification is set forth by way of illustration and not limitation, and that various modifications and changes may be made without departing from the spirit and scope of the present invention.

What is claimed is:

1. A method for the screening of a test compound for inhibiting the binding of a CD4-HIV-1 complex to a chemokine receptor, comprising:
   (a) preparing a magnetic ligand by mixing a magnetic, CD4-containing substrate with HIV-1,
   (b) mixing the magnetic ligand from step (a) with a test compound,
   (c) adding cells that express a chemokine receptor to the mixture from step (b),
   (d) separating cells that bound magnetic ligands from cells without bound magnetic ligands by contact with a magnetic separator, and
   (e) quantifying the cells with bound magnetic ligands and quantifying the cells without bound magnetic ligands.

2. The method of claim 1, wherein the magnetic, CD4-containing substrate is a CD4 magnetic bead.

3. The method of claim 2, wherein the magnetic bead is a paramagnetic divinyl benzene bead.

4. The method of claim 2, wherein the quantifying in step (e) is carried out fluorometrically.

5. The method of claim 2, wherein the quantifying in step (e) is carried out enzymatically.

6. The method of claim 2, wherein the quantifying in step (e) is carried out enzymatically with lactate dehydrogenase.

7. The method of claim 2, wherein the HIV-1 is macrophage-tropic HIV-1 Bal.

8. The method of claim 2, wherein the HIV-1 is macrophage-tropic HIV-1 Ada-M.

9. The method of claim 2, wherein the HIV-1 is T lymphocyte-tropic HIV IIIB.

10. The method of claim 2, wherein the cells that express the chemokine receptor are PM-1 cells.

11. The method of claim 7, wherein the quantifying in step (e) is carried out fluorometrically.

12. The method of claim 8, wherein the quantifying in step (e) is carried out fluorometrically.

13. The method of claim 9, wherein the quantifying in step (e) is carried out fluorometrically.

14. The method of claim 11, wherein the cells that express the chemokine receptor are PM-1 cells.

15. The method of claim 12, wherein the cells that express the chemokine receptor are PM-1 cells.

16. The method of claim 13, wherein the cells that express the chemokine receptor are PM-1 cells.

17. The method of claim 1, wherein the chemokine receptor is selected from the group consisting of fusin, CCR-5, CCR-3 and CCR-2b.

* * * * *